US008838212B2

(12) United States Patent
Klaffenbach

(10) Patent No.: US 8,838,212 B2
(45) Date of Patent: Sep. 16, 2014

(54) APPARATUS AND METHODS FOR ILLUMINATING SUBSTANCES USING COLOR TO ACHIEVE VISUAL CONTRAST

(75) Inventor: David K. Klaffenbach, Imperial, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 586 days.

(21) Appl. No.: 13/108,483

(22) Filed: May 16, 2011

(65) Prior Publication Data

US 2012/0293992 A1 Nov. 22, 2012

(51) Int. Cl.
*A61B 5/05* (2006.01)
*F21V 9/00* (2006.01)
*G01N 21/29* (2006.01)

(52) U.S. Cl.
CPC .................. *G01N 21/29* (2013.01)
USPC ............ 600/476; 600/407; 362/233; 362/232

(58) Field of Classification Search
USPC ........... 362/233, 269, 232, 572; 600/476, 407
See application file for complete search history.

(56) References Cited

U.S. PATENT DOCUMENTS

| | | | |
|---|---|---|---|
| 4,060,724 A * | 11/1977 | Heine et al. | 362/572 |
| 5,351,168 A | 9/1994 | Easley | |
| 5,591,160 A | 1/1997 | Reynard | |
| 5,630,809 A | 5/1997 | Connor | |
| 5,681,264 A | 10/1997 | Ryan, Jr. | |
| 5,785,645 A | 7/1998 | Scheller | |
| 5,916,149 A | 6/1999 | Ryan, Jr. | |
| 6,080,143 A | 6/2000 | Connor | |
| 6,193,650 B1 | 2/2001 | Ryan, Jr. | |
| 6,254,530 B1 | 7/2001 | Ryan, Jr. | |
| 7,654,716 B1 | 2/2010 | Bhadri et al. | |
| 7,704,246 B2 | 4/2010 | Connor | |
| 2008/0137362 A1* | 6/2008 | Gjettermann | 362/572 |
| 2009/0146583 A1 | 6/2009 | Bhadri et al. | |
| 2010/0268202 A1 | 10/2010 | Connor | |

FOREIGN PATENT DOCUMENTS

GB        2 323 162 A        9/1998
WO     WO2004/114647      12/2004

OTHER PUBLICATIONS

Hung, R.W.G. "Measuring Colour," Fountain Press, 3rd Edition 1998, Chapter 1-3; pp. 17-22.
Mary Eng et al, "The Analysis of Metameric Blue Fibers and Their Forensic Significance" Journal of Forensic Sciences, vol. 54, No. 4, Jul. 1, 2009, pp. 841-845.
International Search Report (PCT/ISA/210) and Written Opinion (PCT/ISA/237) mailed on Aug. 31, 2012.
Color Principles-Hue, Saturation, and Value, http://www.ncsu.edu/scivis/lessons/colormodels/color_models2.html, printed May 5, 2011.
Metamerism, http://en. wikipedia.org/wiki/Metamerism_%28colour%29, printed May 9, 2011.

* cited by examiner

*Primary Examiner* — Anabel Ton
(74) *Attorney, Agent, or Firm* — Michael L. Smith

(57) ABSTRACT

An illumination system for illuminating a first biologic substance and a second biologic substance, comprising a first light output device capable of outputting polychromatic first light, a second light output device capable of outputting polychromatic second light, the first light output device and the second light output device selected such that (i) a first apparent color results when the first light is scattered from the first biologic substance and a second apparent color results when the second light is scattered from the first biologic substance, the first apparent color and the second apparent color being substantially the same as one another and (ii) a third apparent color results when the first light is scattered from the second biologic substance and a fourth apparent color results when the second light is scattered from the second biologic substance, the third apparent color and the fourth apparent color being substantially different than one another, and means for temporally modulating amounts of the first light and amounts of the second light in a light output from the system.

19 Claims, 5 Drawing Sheets

APPARATUS AND METHODS FOR ILLUMINATING SUBSTANCES USING COLOR TO ACHIEVE VISUAL CONTRAST

FIELD OF INVENTION

The present invention relates to illumination of substances, and more particularly to illumination of substances using color to achieve visual contrast.

BACKGROUND OF THE INVENTION

A spectrum of light is commonly represented by a chart illustrating a magnitude of light plotted as a function of wavelength. For example, a spectrum may exist for a light output device or light from a light output device after the light has been scattered from a substance.

Color is a physiological response to a spectrum of light. A color may arise from a response to a narrow band spectrum (e.g., monochromatic light) or a broader spectrum of light. For example, color may be a response to a spectrum of a light output device (if the light is directly incident on an eye) or a response to a spectrum that results after the light from the light output device is scattered from a substance (if the light is viewed after the light is incident on the substance).

Perception of a color in response to viewing a spectrum of light results from a brain's interpretation of outputs of an eye's three different types of cones in response to the spectrum. A color that is perceived in response to viewing a spectrum of light is commonly referred to as an apparent color. Since many different spectra can give rise to the same outputs from the cones, a given color can be percieved when any of the different spectra is incident on the eye.

Colors that appear the same but result from different spectra are referred to as metameric colors, or simply metamers.

SUMMARY

Metamaric colors can be achieved, for example, by scattering a first light and a second light from a first substance where the first light and the second light have different spectral components. Illumination of the first substance with the first light and illumination with the second light will give rise to metameric colors if the spectrum of the light scattered by the first substance when illuminated by the first light gives rise to an apparent color that is the same as the apparent color that results when the first substance is illuminated by the second light. As a result, the first substance appears to have the same color regardless of which of the two spectra illuminates the first substance. While metameric colors result from illumination of the first substance with the first light and the second light, if the first light and the second light are scattered from a second substance (i.e., the second substance having different reflectance properties than the first substance), the second substance will appear to have two different colors, the color depending on which of the first light and the second light is used to illuminate the second substance. That is, the first light and second light will not give rise to metameric colors when they are scattered from the second substance.

According to aspects of the present invention, a first light and a second light are chosen such that metamerism is intentionally achieved for a first substance and not achieved for a second substance. Furthermore, flicker photometry (e.g., projecting different amounts of the first light and the second light onto a substance in an alternating manner) may be used to increase an observer's sensitivity to the presence of the first substance and the second substance. For example, in some embodiments, it is appropriate to modulate the light outputs at the rate of 15-20 Hz, a rate at which observers tend to be most sensitive to differences in color. It will be appreciated that during a procedure, at times, the first substance and the second substance will be simultaneously illuminated by the first light and the second light. During simultaneous illumination, one of the substances will appear to have a constant color and the other substance will appear to vary in color depending on whether it is illuminated by the first light or the second light.

It will also be appreciated that in some instances, when metamerism is achieved for light reflected from a given substance, some flicker may occur due to spatial variations in the reflectance properties of a substance. For example, if the substance is retinal tissue, portions of the tissue having blood vessels or greater blood flow may have different reflectance properties than other portions of the tissue. However, for a bulk of the tissue, metamerism will be achieved.

For example, spectra of the first light and the second light to be used in an embodiment of the present invention can be chosen by examining reflectance spectra for a first substance (i.e., a background substance) and for a second substance (i.e., a target substance) and adjusting the spectra of the first light and/or the second light to achieve metamerism for the light scattered from the first substance. A list of pairs of spectra of the first light and second light can thus be obtained, the pairs resulting in a same perceived color when alternately illuminating the first substance, and a substantial color difference when alternately illuminating the second substance.

The term "scatter" as used herein refers to light that is diffusely reflected from a substance.

An aspect of the invention is directed to an illumination system for illuminating a first biologic substance and a second biologic substance, comprising a first light output device capable of outputting polychromatic first light, a second light output device capable of outputting polychromatic second light, the first light output device and the second light output device selected such that (i) a first apparent color results when the first light is scattered from the first biologic substance and a second apparent color results when the second light is scattered from the first biologic substance, the first apparent color and the second apparent color being substantially the same as one another and (ii) a third apparent color results when the first light is scattered from the second biologic substance and a fourth apparent color results when the second light is scattered from the second biologic substance, the third apparent color and the fourth apparent color being substantially different than one another, and means for temporally modulating amounts of the first light and amounts of the second light in a light output from the system.

In some embodiments, at least one of the first light output device and the second light output device comprises a polychromatic source. The first light output device and the second light output device may comprise a common polychromatic source.

In some embodiments, at least one of the first light output device and the second light output device comprises a monochromatic source.

In some embodiments, the means for modulating is adapted to alternately provide the first light and the second light in the light output from the system. In some embodiments, the means for modulating is adapted to alter an amount of the first light and the second light in the light output from the system such that both the first light and the second light are output at a same time.

The means for modulating may comprise an electromechanical component for alternately positioning a first filter and a second filter to form the first light and the second light.

The means for modulating may comprise an electrical component for alternately enabling a first filter and a second filter to form the first light and the second light. The first light output dev ice may comprise a first source and the second light output device may comprise a second source, and the means for modulating may comprise an electrical component for altering an output from a first source and an output from a second source to alter the first light and the second light.

In some embodiments, at least one of the first light output device and the second light output device comprises at least two LEDs.

Another aspect of the invention is directed to a method of illuminating a first biologic substance and a second biologic substance, comprising outputting onto, both, the first biologic substance and the second biologic substance A) a modulated polychromatic first light, and B) a modulated polychromatic second light, (i) scattering of the first light by the first biologic substance giving rise to a first apparent color and scattering of the second light by the first biologic substance giving rise to a second apparent color, the first apparent color and the second apparent color being substantially the same as one another, and (ii) scattering of the first light by the second biologic substance giving rise to a third apparent color and scattering of the second light by the second biologic substance giving rise to a fourth apparent color, the third apparent color and the fourth apparent color being substantially different from one another.

The method may comprise producing at least one of the first light and the second light using a polychromatic source. The step of producing may comprise using the polychromatic source to produce the first light and the second light.

The method may comprise producing at least one of the first light and the second light using a monochromatic source.

The step of outputting may comprise alternately outputting the first light and the second light onto, both, the first biologic substance and the second biologic substance. The step of outputting may comprise modulating an amount of the first light and an amount of the second light such that the first light and the second light are projected onto, both, the first biologic substance and the second biologic substance at a same time.

The step of outputting may comprise alternately positioning a first filter and a second filter in a light from a source to form the first light and the second light.

The step of outputting may comprise using an electrical component to enable a first filter and a second filter to form the first light and the second light.

The step of outputting comprises altering an amount of light output from a first source and an amount of light output from a second source.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1A:
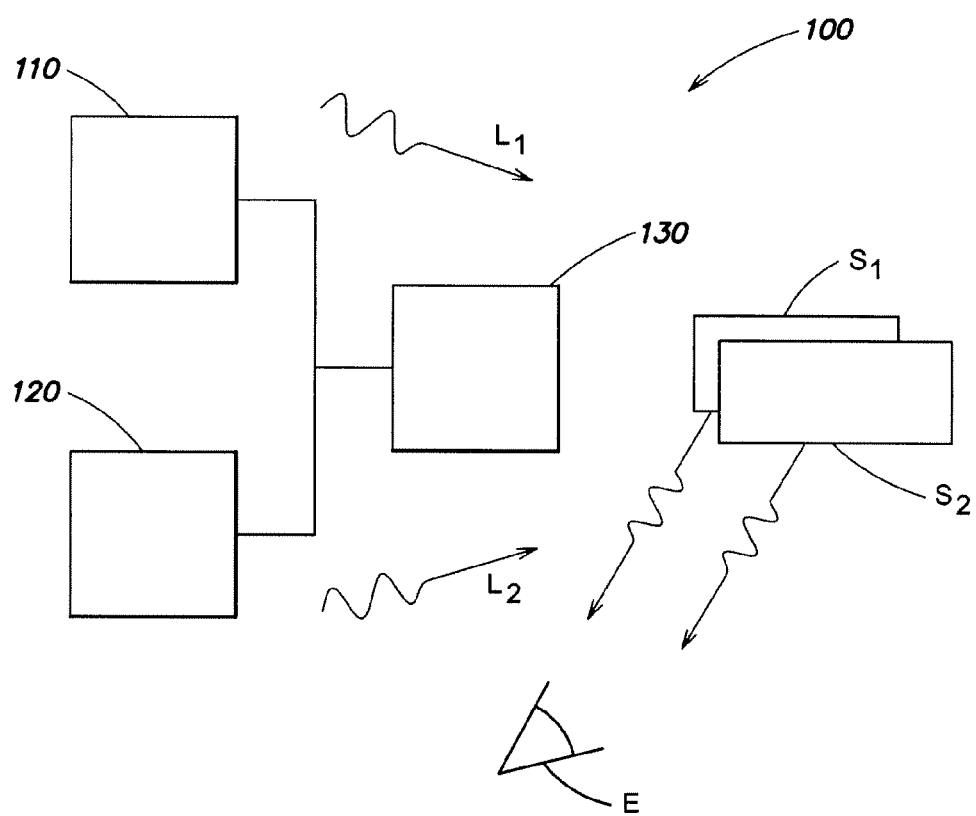
FIG. 1A is a block diagram of an illumination system according to aspects of the present invention for illuminating substances.

FIG. 1A is a block diagram of an illumination system 100 for illuminating a first substance $S_1$ and a second substance $S_2$. The illumination system comprises a first light output device 110 for producing first polychromatic light $L_1$, a second light output device 120 for producing second polychromatic light $L_2$ and means 130 for temporally modulating amounts of first light $L_1$ and amounts of second light $L_2$ in a light output from system 100.

First light output device 110 is capable of producing first light $L_1$ comprising at least light of a first wavelength and light of a second wavelength. It will be appreciated that first light $L_1$ generates a first apparent color after it is scattered from first biologic substance $S_1$ and a second apparent color after it is scattered from the second biologic substance $S_2$.

For example, the first light output device may comprise a polychromatic source, or the first light output device may comprise two or more sources of light each providing a different color component than the other. In embodiments having two or more sources, the outputs of the two or more sources are combined to produce the first light which has a polychromatic spectrum; and, each source can be monochromatic or polychromatic. For example, in embodiments including monochromatic sources, the first light output device may comprise two or more LEDs each providing light of a different color or the output device may comprise two or more lasers each providing light of a different color. For example, in embodiments comprising a polychromatic source, which may be filtered or unfiltered, the first light output device may comprise one or more gaseous arc lamp or incandescent lamp.

Second light output device 120 is capable of producing second light $L_2$. Second light output device 120 may be configured in any manner as set forth above with reference to first light output device 110 provided that the conditions for the first light and second light, as set forth herein, are met.

It will be appreciated that, although the above embodiments were described as forming the first light and the second light from different sources, the first light and the second light can be obtained by selectively filtering portions of the spectrum of a single polychromatic source.

First light output device 110 and the second light output device 120 are selected such that (i) a first apparent color results when the first light $L_1$ is scattered from the first substance $S_1$ and observed by eye E, and a second apparent color results when the second light $L_2$ is scattered from the first substance $S_1$ and observed by eye E, the first apparent color and the second apparent color being substantially the same as one another.

Additionally, first light output device 110 and the second light output device 120 are selected such that (ii) a third apparent color results when the first light $L_1$ is scattered from the second substance $S_2$ and a fourth apparent color results when the second light $L_2$ is scattered from the second substance $S_2$, the third apparent color and the fourth apparent color being substantially different than one another. It will be appreciated that second substance $S_2$ will appear to have a first color when illuminated by the first light $L_1$ and will appear to have a second color when illuminated by the second light $L_2$; whereas the first substance $S_1$ will appear to have a same color regardless of whether the first substance is illuminated by the first light $L_1$ or the second light $L_2$. The first apparent color and the second apparent color will be of a same hue as one another (e.g., red, yellow, green, blue, or an intermediate thereof). It is also advantageous that the first apparent color and the second apparent color have a same or very similar value and saturation such that a viewer sees a substance as a constant color, when the substance is alternately illuminated by the first light and the second light. Typically, the third apparent color and the fourth apparent color will be of different hues than one another. However, the third apparent color and the fourth apparent color may be of a same hue as one another provided they have substantially different values and/or saturation such that a color contrast is visible when the substance is alternately illuminated by the first light and the second light.

Means 130 for temporally modulating amounts of the first light $L_1$ and the second light $L_2$ in a light output from system 100 alters the relative amounts of first light $L_1$ and second light $L_2$ in the output. Typically the peak amounts of $L_1$ and $L_2$ will occur at different times. For example, the $L_1$ and $L_2$ may be periodic signals that are out of phase (e.g. by 180 degrees).

Means 130 may be embodied in numerous ways. For example, means 130 may be embodied as a mechanically movable part that alternately directs first light $L_1$ and second light $L_2$ into the output of system 100. Alternatively, the means alters the amount of first light $L_1$ and second light $L_2$ in the output. The means may comprise one or more optical components such a mirror or a refractive element. For example, the optical component may be rotatable mirror, a digital mirror or an acousto-optical component.

As indicated above, in some embodiments, the first light and the second light are formed by filtering a single broadband source. In such embodiments, the first light output device comprises the broadband source and a first filter and the second light output device comprises the broadband light source, which may be unfiltered or may be filtered by a second filter.

It will be appreciated that, in such embodiments, by alternately filtering light from the broadband source it is possible to form a first light and a second light as described above. It will also be appreciated that, in some such embodiments, the means for temporally modulating a light output consists of an electromechanical component (i.e., no optical component) for alternately positioning the first filter and the, optional, second filter which are parts of the first light output device and the second light output device, respectively. For example, the first filter and the second filter may be located on a filter wheel which causes the light from the source to be alternately filtered by the first filter and the second filter.

In other such embodiments, where a filter material may be electrically alterable or alterable by other stimulus to provide differing filtering properties, the means 130 for temporally modulating a light output consists of an electrical or other non-mechanical component for alternately providing or enabling the first filter and the second filter. As indicated above, the first filter and the second filter are parts of the first light output device and the second light output device, respectively.

In yet other such embodiments, two light sources providing first light and second light, respectively, are modulated each with or without filtering. The means for temporally modulating a light output of system 100 consists of an electrical device for modulating (e.g., alternately activating) the first light source and the second light source. In any given embodiment, means 130 may comprise one or more optical, mechanical, electrical or other components.

The wavelength components of first light $L_1$ and second light $L_2$ can be selected experimentally by adding to or subtracting from the spectrum of light $L_1$ and/or $L_2$ while observing first substance $S_1$, and adjusting the components until the first substance $S_1$ appears to have the same color when illuminated by either first light $L_1$ or second light $L_2$. Of course, it will be appreciated that spectra of the first light and the second light must be different than one another. Additionally, second substance $S_2$ must appear to have different colors depending on whether the second substance is illuminated by first light $L_1$ or second light $L_2$. It will also be appreciated that, provided the compositions of the substances $S_1$ and $S_2$ are different that, after having selected the spectral components of the first light $L_1$ and second light $L_2$ such that the first substance $S_1$ appears to have the same color regardless of which light is used to illuminate the first substance, in most instances it is a trivial matter that second substance $S_2$ must appear to have different colors depending on whether the second substance is illuminated by first light $L_1$ or second light $L_2$.

Alternatively, the wavelength components of first light $L_1$ and second light $L_2$ can be calculated or calculated to achieve a starting point for experimental selection. Calculation can be achieved using conventional color reproduction techniques, such as those described in Measuring Colour, by Dr. R. W. G. Hunt, Third Edition, Fountain Press, ISBN 0 86343 387 1 the substance of which is incorporated by reference. For example, it will be appreciated that calculations to determine light outputs for first light $L_1$ and second light $L_2$ when scattered from a substance typically include multiplying a reflectance curve for the substance (e.g., a reflectance curve of retinal tissue) by the spectrum of lights $L_1$ to achieve a first result and multiplying the reflectance curve for the substance by the spectrum of lights $L_2$ to achieve a second result. A gain may then be selected for one or both of the results to facilitate achieving the same or similar light amplitudes for the first and second outputs. It will be appreciated that the gain will typically be selected such that the light amplitude (in addition to the reflected color) does not cause substantial flicker in light intensity when a substance is viewed by a user of the system as it is alternately illuminated by $L_1$ and $L_2$. After the gain applied, the resulting spectra may be multiplied by color matching functions and normalized.

The substances $S_1$, $S_2$ may be biologic or non-biologic. Biologic substances may be human or non-human. The biologic substances may be from any internal or external portion of a human body. For example, the biologic substances may be ophthalmic substances. For example, the first substance may be retinal tissue and the second substance may be vitreous humor. Either of the biologic substances may be tissue or non-tissue.

First light output device 110 and second light output device 120 may directly illuminate the first substance $S_1$ and/or second substance $S_2$, or may be conducted through one or more optical elements such as a fiber optic.

Figure 1B:
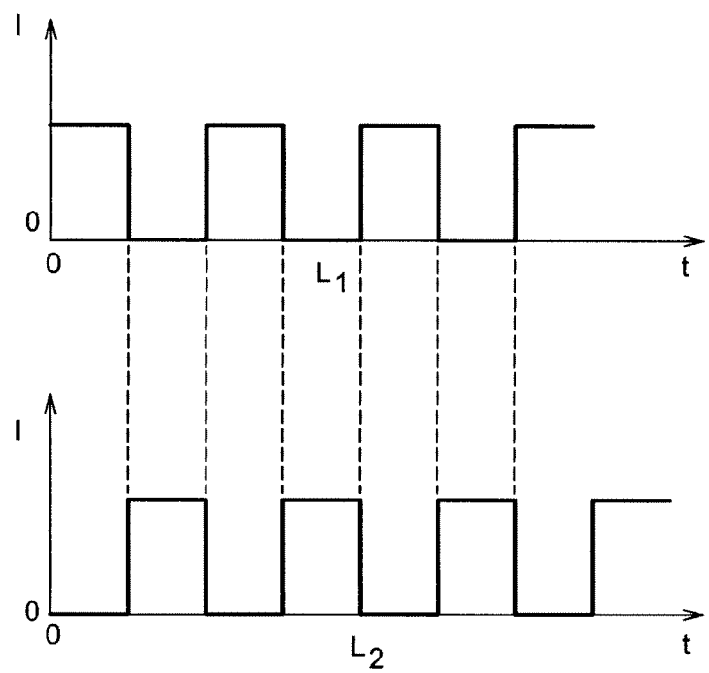
FIGS. 1B and 1C are graphical representations of light signals showing modulations of amplitudes of light $L_1$ and light $L_2$.
Figure 1C:
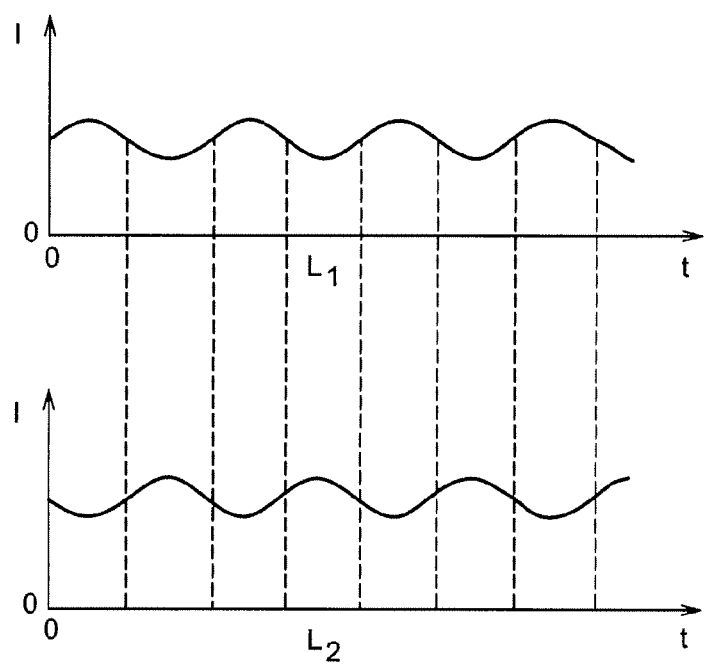

FIGS. 1B and 1C are graphical representations of periodic light amplitude signals showing modulations of light $L_1$ and light $L_2$. The graphs indicate light amplitude (e.g., intensity) as a function of time. In FIG. 1B, the signals of light $L_1$ and light $L_2$ are square waves where light $L_1$ and light $L_2$ are alternately provided in the output of system 100. That is, each of light $L_1$ and light $L_2$ are fully on and fully off, and signals are out of phase with one another (e.g, 180 degrees out of phase). In FIG. 1C, the amounts of light in the system output are altered; however neither light $L_1$ and light $L_2$ is not completely off over the illustrated time period t. It will be appreciated that in such a configuration, the amount of flicker can be set to an amount that is visible yet not unpleasant. It will also be appreciated that a non-square wave signal may be used (e.g., a sinusoidal wave) to control the amount of flicker observed by a user.

Figure 2:
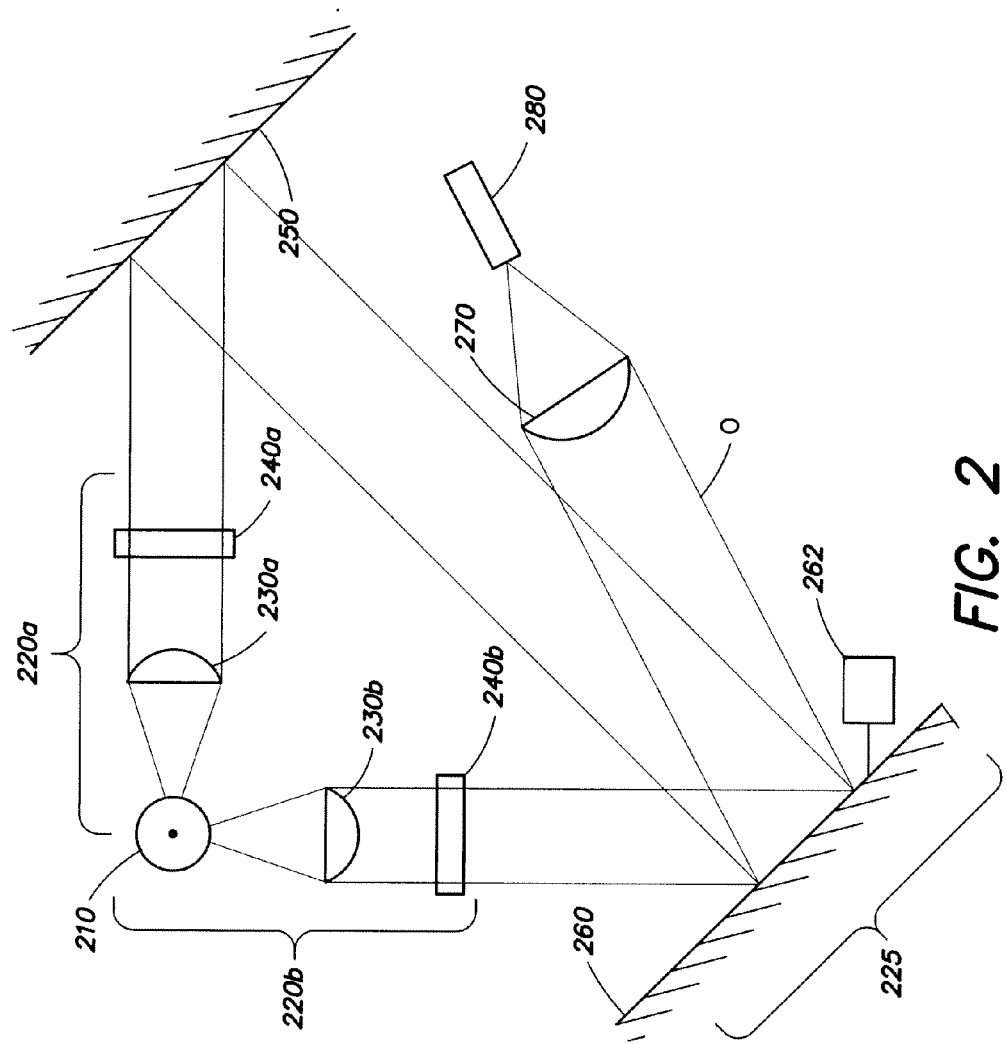
FIG. 2 is a schematic illustration of an example of an embodiment of an illumination system for illuminating substances, according to aspects of the present invention.
Figure 3:
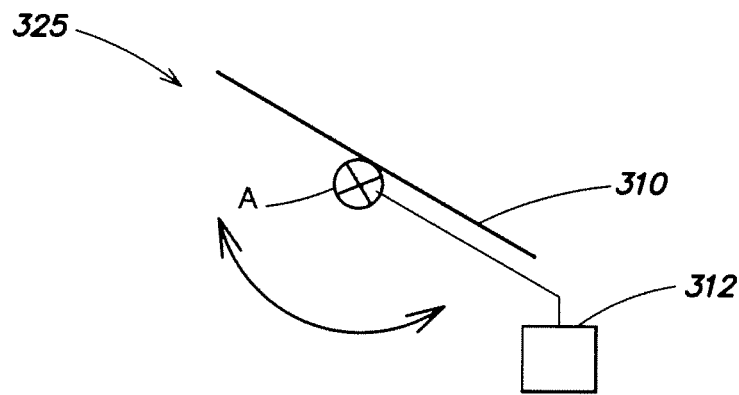
FIG. 3 is a schematic illustration of an example of a means for temporally modulating a light output for use in illumination systems for illuminating substances, according to aspects of the present invention.

FIG. 2 is a schematic illustration of an example of an embodiment of an illumination system for illuminating substances, according to aspects of the present invention. In the illustrated embodiment, a first light output device 220*a* comprises a broadband light source 210 and a filter 240*a*, and a second light output device 220*b* comprises broadband light source 210 and a filter 240*b*. As illustrated, devices 220*a* and 220*b* may comprise one or more collimating optics 230*a* and 230*b*, and one or more steering optics (e.g., mirror 250). A means 225 for temporally modulating a light output includes a digital mirror 260 and appropriate controls 262 for selectively directing light from output device 220*a* and light from output device 220*b* into output path O. Optionally, the output path may include a fiber optic 280, and corresponding focusing optics 270 for delivering the light to substances. For example, a fiber optic may be desirable where light is to be delivered inside a human body, for example, into an eye. FIG. 3 illustrates an example of a means 325 for temporally modulating amounts of first light $L_1$ and the second light $L_2$ in the light output from system 100. Means 325 comprises a conventional planar mirror 310 which is rotatable about an axis A by a drive mechanism 312. Means 325 can replace means 225 in the system of FIG. 2, and selectively direct light from output device 220*a* and light from output device 220*b* into output path O.

Figure 4:
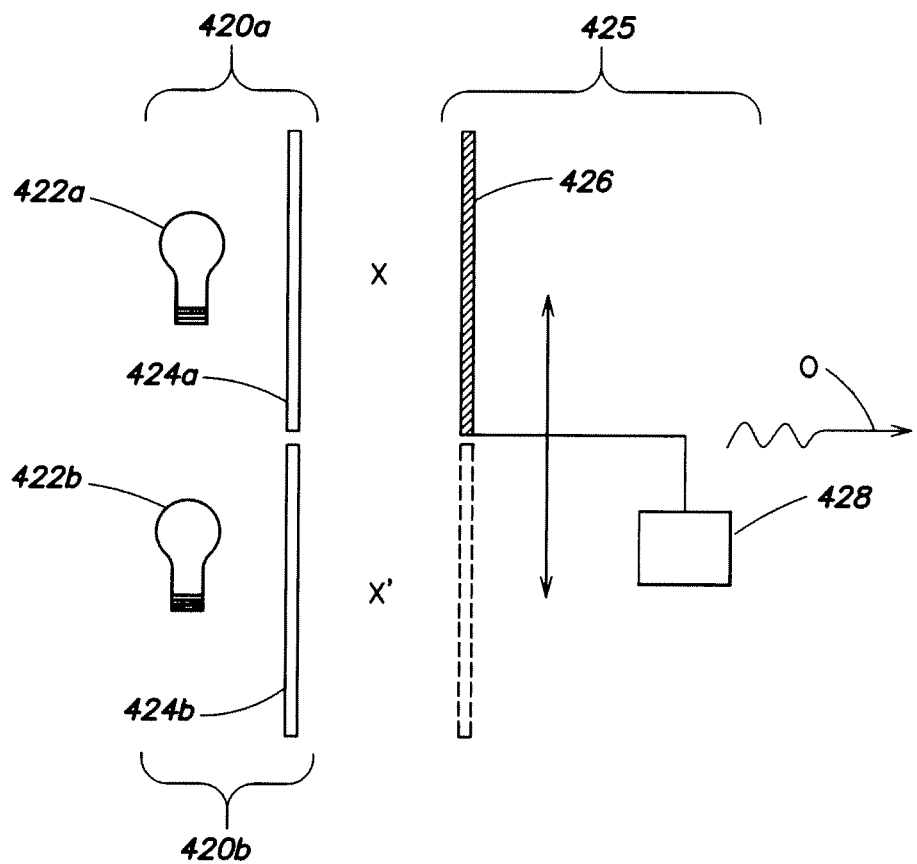
FIGS. 4-6 are schematic illustrations of examples of light output devices and means for temporally modulating a light output for use in illumination systems for illuminating substances, according to aspects of the present invention.

FIG. 4 is schematic illustration of examples of light output devices 420*a*, 420*b* and means 425 for temporally modulating a light output for use in illumination systems for illuminating substances, according to aspects of the present invention. In the illustrated embodiment, first light output device 420*a* comprises a first broadband source 422*a* and a first filter 424*a* for generating first light; and second light output device 420*b* comprises a second broadband source 422*b* and a second filter 424*b* for generating second light. Means 425 for temporally modulating a light output O comprises an opaque shutter 426 and a driver 428 for moving the shutter between a first position X and a second position X' where it alternately blocks light from one of the light output devices 420*a*, 420*b* and permits light to enter the output O from the other light output device 420*a* and 420*b*. In some embodiments, to achieve signals of light $L_1$ and $L_2$ as shown in FIGS. 1B or 1C, shutter 426 may be less than fully opaque or shutter 426 may be configured to so as to not completely block light form device 420*a* when in position X, and not completely block light from device 420*b* when in position X.

Figure 5:
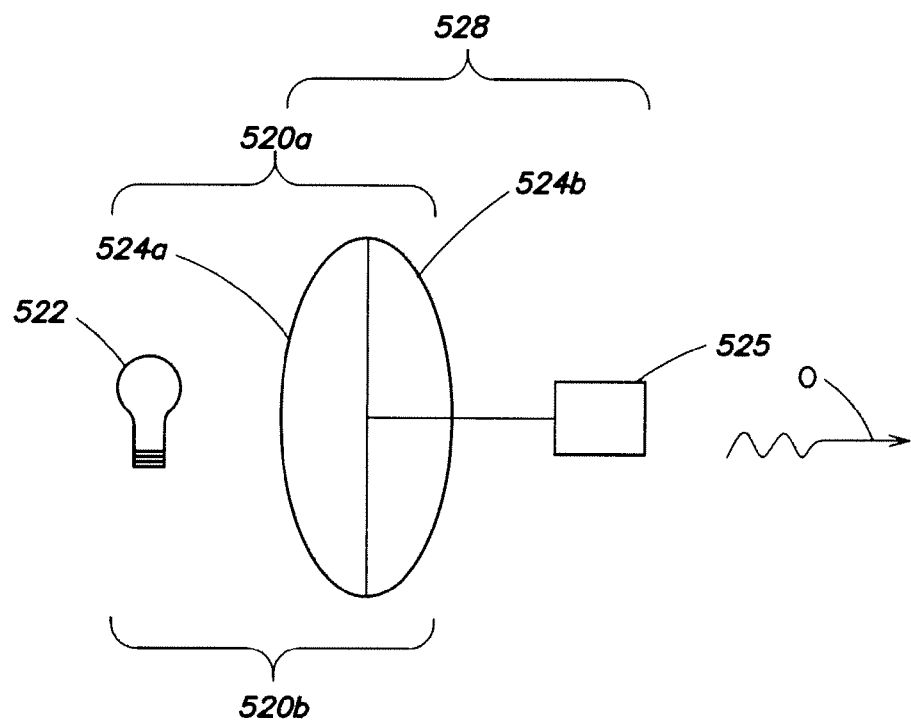

FIG. 5 is a schematic illustration of examples of light output devices 520*a*, 520*b* and means 525 for temporally modulating a light output for use in illumination systems for illuminating substances, according to aspects of the present invention. In the illustrated embodiment, first light output device 520*a* comprises a broadband source 522 and a first filter 524*a* for generating first light; and second light output device 520*b* comprises broadband source 522 and a second filter 524*b* for generating second light. Means 525 for temporally modulating a light output O comprises an rotatable structure for alternately positioning first filter 524*a* and second filter 524*b* in front of source 522 and a driver 528 for rotating the structure such that the light from source 522 is alternately filtered by the first filter 524*a* and second filter 524*b* before entering output O. Output O may comprise one or more optics for delivering light to substances (e.g., fiber optics, steering optics or focusing optics).

Figure 6:
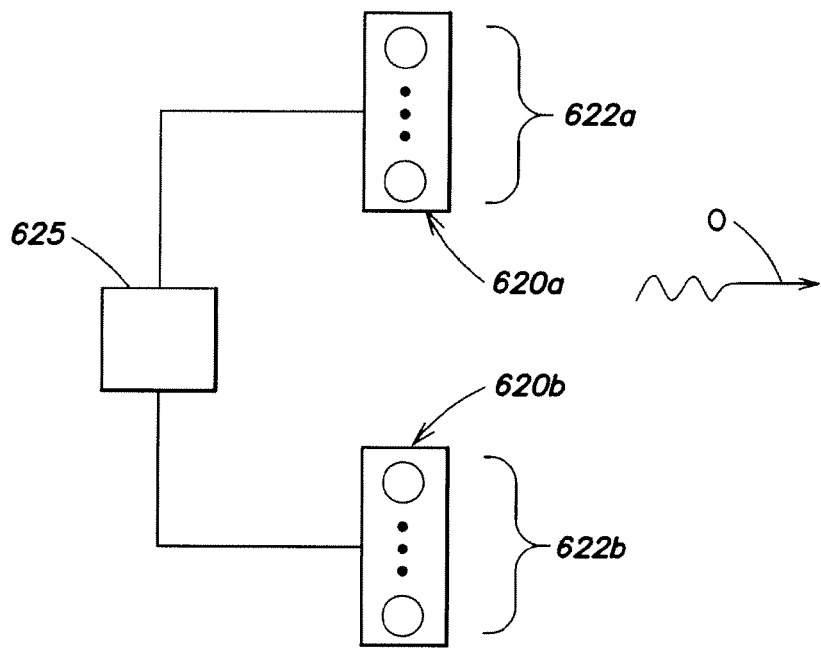

FIG. 6 is a schematic illustration of examples of light output devices 620*a*, 620*b* and means 625 for modulating amounts of the first light $L_1$ and the second light $L_2$ in a light output O for use in illumination systems for illuminating substances, according to aspects of the present invention. In the illustrated embodiment, first light output device 620*a* for producing polychromatic light $L_1$ comprises a first plurality of monochromatic sources $622a_{1-n}$ for generating first light $L_1$; and second light output device 620*b* for producing polychromatic light $L_2$ comprises a second plurality of monochromatic sources $622b_{1-n}$ for generating the second light $L_2$. For example, sources 622*a* and/or sources 622*b* may comprise two or more LEDs. Means 625 for modulating amounts of the first light $L_1$ and the second light $L_2$ in a light output comprises an electronic driver for modulating device 620*a* and device 620*b*. Devices 620*a* and 620*b* may comprise one or more filters. Output O may comprise one or more optics for delivering light to substances (e.g., fiber optics, steering optics or focusing optics).

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

I claim:

1. An illumination system for illuminating a first biologic substance and a second biologic substance, comprising:
    a first light output device capable of outputting polychromatic first light;
    a second light output device capable of outputting polychromatic second light, the first light and the second light having different spectra with respect to each other and selected such that (i) a first apparent color results when the first light is scattered from the first biologic substance and a second apparent color results when the second light is scattered from the first biologic substance, the first apparent color and the second apparent color being substantially the same as one another and (ii) a third apparent color results when the first light is scattered from the second biologic substance and a fourth apparent color results when the second light is scattered from the second biologic substance, the third apparent color and the fourth apparent color being substantially different than one another; and
    means for temporally modulating amounts of the first light and amounts of the second light in a light output from the system.

2. The system of claim 1, wherein at least one of the first light output device and the second light output device comprises a polychromatic source.

3. The system of claim 1, wherein the first light output device and the second light output device comprise a common polychromatic source.

4. The system of claim 1, wherein at least one of the first light output device and the second light output device comprises a monochromatic source.

5. The system of claim 1, wherein the means for modulating is adapted to alternately provide the first light and the second light in the light output from the system.

6. The system of claim 1, wherein the means for modulating is adapted to alter an amount of the first light and the second light in the light output from the system such that both the first light and the second light are output at a same time.

7. The system of claim 1, wherein means for modulating comprises an electromechanical component for alternately positioning a first filter and a second filter to form the first light and the second light.

8. The system of claim 1, wherein means for modulating comprises an electrical component for alternately enabling a first filter and a second filter to form the first light and the second light.

9. The system of claim 1, wherein the first light output device comprises a first source and the second light output device comprises a second source, and wherein the means for modulating comprises an electrical component for altering an output from a first source and an output from a second source to alter the first light and the second light.

10. The system of claim 1, wherein at least one of the first light output device and the second light output device comprises at least two LEDs.

11. A method of illuminating a first biologic substance and a second biologic substance, comprising:
outputting onto, both, the first biologic substance and the second biologic substance A) a modulated polychromatic first light, and B) a modulated polychromatic second light,
(i) scattering of the first light by the first biologic substance giving rise to a first apparent color and scattering of the second light by the first biologic substance giving rise to a second apparent color, the first apparent color and the second apparent color being substantially the same as one another, and
(ii) scattering of the first light by the second biologic substance giving rise to a third apparent color and scattering of the second light by the second biologic substance giving rise to a fourth apparent color, the third apparent color and the fourth apparent color being substantially different from one another.

12. The method of claim 11, further comprising producing at least one of the first light and the second light using a polychromatic source.

13. The method of claim 12, wherein the step of producing comprises using the polychromatic source to produce the first light and the second light.

14. The method of claim 11, further comprising producing at least one of the first light and the second light using a monochromatic source.

15. The method of claim 11, wherein the step of outputting comprises alternately outputting the first light and the second light onto, both, the first biologic substance and the second biologic substance.

16. The system of claim 11, wherein the step of outputting comprises modulating an amount of the first light and an amount of the second light such that the first light and the second light are projected onto, both, the first biologic substance and the second biologic substance at a same time.

17. The system of claim 11, wherein the step of outputting comprises alternately positioning a first filter and a second filter in a light from a source to form the first light and the second light.

18. The system of claim 11, wherein the step of outputting comprises using an electrical component to enable a first filter and a second filter to form the first light and the second light.

19. The system of claim 11, wherein the step of outputting comprises altering an amount of light output from a first source and an amount of light output from a second source.

* * * * *